United States Patent
Shute et al.

(10) Patent No.: US 12,144,591 B2
(45) Date of Patent: Nov. 19, 2024

(54) BODY VIBRATION ANALYSIS SYSTEMS AND METHODS

(71) Applicant: Cardiac Pacemakers, Inc., St. Paul, MN (US)

(72) Inventors: Jonathan Bennett Shute, Eagan, MN (US); John D. Hatlestad, Maplewood, MN (US); John H. Tangren, Lino Lakes, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 388 days.

(21) Appl. No.: 17/190,277

(22) Filed: Mar. 2, 2021

(65) Prior Publication Data
US 2021/0275039 A1 Sep. 9, 2021

Related U.S. Application Data

(60) Provisional application No. 62/985,137, filed on Mar. 4, 2020.

(51) Int. Cl.
*A61B 5/0205* (2006.01)
*A61B 5/00* (2006.01)
(Continued)

(52) U.S. Cl.
CPC .......... *A61B 5/0205* (2013.01); *A61B 5/0064* (2013.01); *A61B 5/02427* (2013.01); *A61B 5/0806* (2013.01); *A61B 5/7285* (2013.01)

(58) Field of Classification Search
CPC . A61B 5/0205; A61B 5/0064; A61B 5/02427; A61B 5/0806; A61B 5/7285
See application file for complete search history.

(56) References Cited

U.S. PATENT DOCUMENTS 5,563,787 A * 10/1996 Murayama ........... G05D 1/0246
356/152.3
5,768,421 A 6/1998 Gaffin et al.
(Continued)

OTHER PUBLICATIONS

Aasmul, Søren "CARDIS clinical feasibility study initiated," Video published Sep. 25, 2018 accessible at URL<www.cardis.h2020.eu/2019/09/25/cardis-clinical-feasibility-study-initiated/> (4 pages).
(Continued)

*Primary Examiner* — Dixomara Vargas
(74) *Attorney, Agent, or Firm* — Pauly, DeVries Smith & Deffner LLC

(57) ABSTRACT

Embodiments herein relate to body vibration analysis systems and methods. In an embodiment, a body vibration analysis system is included having a first light source configured to illuminate a surface of the body from a first angle with a first set of lighted features and a second light source configured to illuminate a surface of the body from a second angle with a second set of lighted features, wherein the second set of lighted features are optically distinguishable from the first set of lighted features. The system further includes a camera configured to detect light reflected from the surface of the body and a control circuit configured to receive an input from the camera and assess spatial vibration as a function of location on the surface of the body. Other embodiments are also included herein.

19 Claims, 12 Drawing Sheets

(51) Int. Cl.
*A61B 5/024* (2006.01)
*A61B 5/08* (2006.01)

(56) References Cited

U.S. PATENT DOCUMENTS

| | | | | |
|---|---|---|---|---|
| 7,343,278 | B2 | 3/2008 | Billinghurst et al. | |
| 7,676,253 | B2* | 3/2010 | Raridan, Jr. | A61B 5/14552 |
| | | | | 600/323 |
| 8,988,662 | B1* | 3/2015 | Haskin | G01C 3/08 |
| | | | | 356/9 |
| 9,262,840 | B2 | 2/2016 | Schreier | |
| 9,269,022 | B2 | 2/2016 | Rhoads et al. | |
| 2006/0045337 | A1 | 3/2006 | Shilman et al. | |
| 2009/0318815 | A1* | 12/2009 | Barnes | A61B 5/444 |
| | | | | 382/128 |
| 2009/0326383 | A1* | 12/2009 | Barnes | A61B 5/417 |
| | | | | 850/1 |
| 2010/0281986 | A1* | 11/2010 | Toal | G01H 9/00 |
| | | | | 73/656 |
| 2014/0039309 | A1* | 2/2014 | Harris | A61B 5/6803 |
| | | | | 600/431 |
| 2014/0046291 | A1* | 2/2014 | Harris | A61M 5/16836 |
| | | | | 604/503 |
| 2014/0340362 | A1* | 11/2014 | Spears | G06F 3/0418 |
| | | | | 345/175 |
| 2017/0176336 | A1* | 6/2017 | Dimitriadis | G01N 21/6428 |
| 2017/0281009 | A1 | 10/2017 | Obropta, Jr. et al. | |
| 2017/0286809 | A1 | 10/2017 | Pankanti et al. | |
| 2017/0337412 | A1* | 11/2017 | Bhat | A61B 5/1172 |
| 2019/0060026 | A1* | 2/2019 | Geerlings | A61B 90/39 |
| 2019/0096057 | A1* | 3/2019 | Allen | G01N 21/8851 |
| 2019/0254143 | A1* | 8/2019 | Hallack | F21V 21/30 |
| 2020/0121262 | A1* | 4/2020 | De Haan | A61B 5/7285 |
| 2020/0284880 | A1* | 9/2020 | Bartlett | G02B 26/06 |
| 2022/0015710 | A1* | 1/2022 | Lewis | A61B 5/706 |
| 2022/0117094 | A1* | 4/2022 | Prest | C04B 35/119 |
| 2022/0257201 | A1* | 8/2022 | Roh | A61B 6/4275 |

OTHER PUBLICATIONS

"CARDIS Early stage CARdio Vascular Disease Detection with Integrated Silicon Photonics," General Presentation dated Jul. 7, 2017 accessible at URL <http://www.cardis-h2020.eu/wp-content/uploads/2017/07/CARDIS-General-Presentation_2017.07.07.pdf> (15 pages).

Carlson, Joe "Medtronic talks robots as it beats earnings estimates, hikes guidance," Star Tribune Article published Aug. 20, 2019 (2 pages).

"Doctors, the WHO and the CARDIS," The Engineer Article Published Jul. 5, 2017 available at URL <https://www.theengineer.co.uk/doctors-the-who-and-the-cardis/> (3 pages).

"New handheld scanner to give instant heart disease diagnosis," Medical Xpress article by Photonics21, published Jul. 4, 2017 accessible at URL <https://medicalxpress.com/news/2017/07-handheld-scanner-instant-heart-disease.html> (4 pages).

"Polytec Laser Vibrometers," Polytec product information available at URL<www.polytec.com/us> at least as early as Dec. 4, 2019 (4 pages).

Puurtinen, Merja et al., "Best Electrode Locations for a Small Bipolar ECG Device: Signal Strength Analysis of Clinical Data," Annals of Biomedical Engineering, vol. 37, No. 2, Feb. 2009, pp. 331-336 (6 pages).

"VIC-3D Overview," Correlated Solutions VIC-3D product information accessible at URL <http://www.correlatedsolutions.com/vic-3d/> at least as early as Nov. 4, 2020 (5 pages).

York, Michele K. et al., "Relationship between Neuropsychological Outcome and DBS Surgical Trajectory and Electrode Location," J Neurol Sci. Dec. 15, 2009; 287(1-2): 159-171 (38 pages).

* cited by examiner

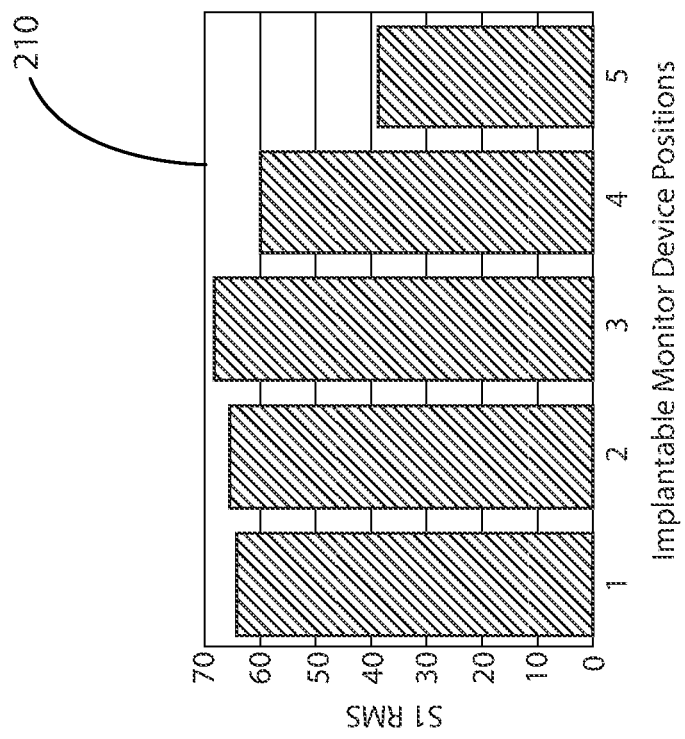
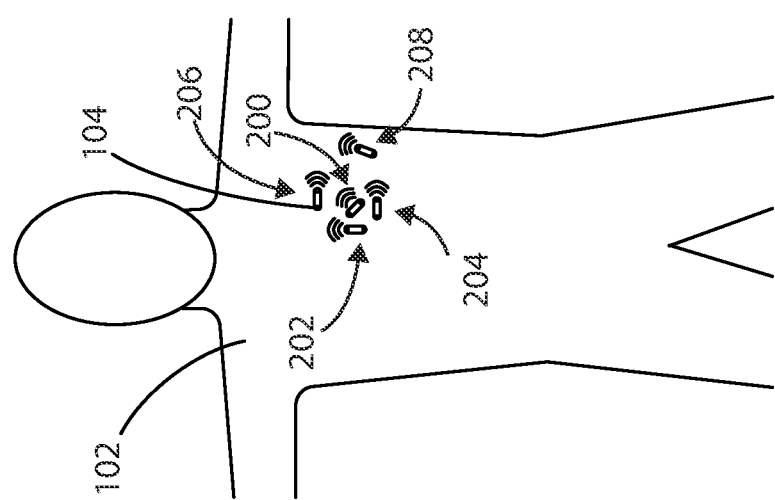
FIG. 2

BODY VIBRATION ANALYSIS SYSTEMS AND METHODS

This application claims the benefit of U.S. Provisional Application No. 62/985,137, filed Mar. 4, 2020, the content of which is herein incorporated by reference in its entirety.

FIELD

Embodiments herein relate to body vibration analysis systems and methods.

BACKGROUND

Implantable medical devices are often used to provide treatment or therapy to patients. Implantable medical devices are also increasingly being used as monitoring devices. Many different physiological parameters can be monitored such as heart rate, heart rhythm, heart sounds, and the like.

As advances are made in medical device therapies, implantable medical devices continue to get smaller and smaller. However, differences in anatomy and physiology of a subject, including bone density, fat distribution, organ size variability, weight, height, the presence of additional implants, and the like, can confound monitoring by smaller medical devices due to vibrational conduction of various physiological signals at the implant site.

SUMMARY

In a first aspect, a body vibration analysis system is included having a first light source configured to illuminate a surface of the body from a first angle with a first set of lighted features, a second light source configured to illuminate a surface of the body from a second angle with a second set of lighted features. The second set of lighted features are optically distinguishable from the first set of lighted features. The system further includes a camera configured to detect light reflected from the surface of the body and a control circuit configured to receive an input from the camera and assess spatial vibration as a function of location on the surface of the body.

In a second aspect, in addition to one or more of the preceding or following aspects, or in the alternative to some aspects, wherein the first set of lighted features are at least one of a different color than the second set of lighted features, a different shape than the second set of lighted features, or a different intensity than the second set of lighted features.

In a third aspect, in addition to one or more of the preceding or following aspects, or in the alternative to some aspects, wherein the control circuit is further configured to generate a body surface map as a function of determined spatial vibration.

In a fourth aspect, in addition to one or more of the preceding or following aspects, or in the alternative to some aspects, wherein the first angle and the second angle intersect at an angle of about 10 to 45 degrees.

In a fifth aspect, in addition to one or more of the preceding or following aspects, or in the alternative to some aspects, wherein the control circuit is further configured to calculate a location for sensing vibrations within a particular frequency range based on the determined spatial vibration as a function of location on the surface of the body.

In a sixth aspect, in addition to one or more of the preceding or following aspects, or in the alternative to some aspects, wherein the control circuit is further configured to calculate a location for implanting a medical device based on the determined spatial vibration as a function of location on the surface of the body.

In a seventh aspect, in addition to one or more of the preceding or following aspects, or in the alternative to some aspects, wherein the control circuit is further configured to diagnose a disease state based on the determined spatial vibration as a function of location on the surface of the body.

In an eighth aspect, in addition to one or more of the preceding or following aspects, or in the alternative to some aspects, wherein the control circuit is further configured to average spatial vibration as a function of location on the surface of the body over a plurality of physiological vibration cycles.

In a ninth aspect, in addition to one or more of the preceding or following aspects, or in the alternative to some aspects, the physiological vibration cycles can include at least one of cardiac cycles and pulmonary cycles.

In a tenth aspect, in addition to one or more of the preceding or following aspects, or in the alternative to some aspects, further can include a sensor, wherein the control circuit is further configured to use a signal from the sensor to separate and align spatial vibration data representing different physiological vibration cycles.

In an eleventh aspect, in addition to one or more of the preceding or following aspects, or in the alternative to some aspects, the sensor can include an ECG sensor.

In a twelfth aspect, an implant location calculating system is included. The system includes a digital image correlation body surface analysis system and a control circuit. The control circuit is configured to receive input from the body analysis system including spatial vibration as a function of location on the surface of the body and calculate a location for implanting a medical device based on the spatial vibration as a function of location on the surface of the body.

In a thirteenth aspect, a method of evaluating body vibrations is included. The method includes illuminating a surface of a subject's body from a first angle with a first set of lighted features, illuminating a surface of a subject's body from a second angle with a first set of lighted features, detecting light reflected from the surface of the subject's body, and calculating spatial vibration as a function of location on the surface of the subject's body based on the detected light.

In a fourteenth aspect, in addition to one or more of the preceding or following aspects, or in the alternative to some aspects, wherein the first set of lighted features are at least one of a different color than the second set of lighted features, a different shape than the second set of lighted features, and a different intensity than the second set of lighted features.

In a fifteenth aspect, in addition to one or more of the preceding or following aspects, or in the alternative to some aspects, the method further can include generating a body surface map as a function of determined spatial vibration.

In a sixteenth aspect, in addition to one or more of the preceding or following aspects, or in the alternative to some aspects, wherein the first angle and the second angle intersect at an angle of about 10 to 45 degrees.

In a seventeenth aspect, in addition to one or more of the preceding or following aspects, or in the alternative to some aspects, the method further can include calculating a location for sensing vibrations within a particular frequency range based on the determined spatial vibration as a function of location on the surface of the subject's body.

In an eighteenth aspect, in addition to one or more of the preceding or following aspects, or in the alternative to some aspects, the method further can include averaging spatial vibration as a function of location on the surface of the subject's body over a plurality of physiological vibration cycles.

In a nineteenth aspect, in addition to one or more of the preceding or following aspects, or in the alternative to some aspects, the physiological vibration cycles can include at least one of cardiac cycles and pulmonary cycles.

In a twentieth aspect, in addition to one or more of the preceding or following aspects, or in the alternative to some aspects, the method further can include using a signal from a sensor to separate and align spatial vibration data representing different physiological vibration cycles, the sensor can include an ECG sensor.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which:

FIG. 2 is a schematic view illustrating different degrees of vibration at different positions in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, implantable medical devices are increasingly being used as monitoring devices. However, implanted monitoring devices can be sensitive to device placement within a patient making monitoring susceptible to low signal to noise ratio and noise interference from more than one signal source.

Multiple body systems, including but not limited to the cardiovascular system, the pulmonary system, and the gastrointestinal system, can generate vibratory signals that can be sensed on the skin surface of a subject by an implanted monitor device. Exemplary vibratory signals can include pulse wave and heart sounds in the cardiovascular system, respiration and lung sounds from the pulmonary system, and peristalsis from the gastrointestinal system. The vibratory signals generated by these various body systems can vary in intensity at a given location on the body surface and can vary from person to person based on differences in anatomy and physiology. As such, precise placement can be important to maximize signal to noise ratio and/or to limit noise interference from other non-targeted sources of vibration.

The systems and methods herein can be used to elucidate the spatio-temporal distribution of the various vibratory signals so as to select an optimal location for implantation of an implantable monitor device. Placement of an implantable monitor device using the devices and methods herein can optimize the signal to noise ratio of a single vibratory signal at any given location.

Figure 1:
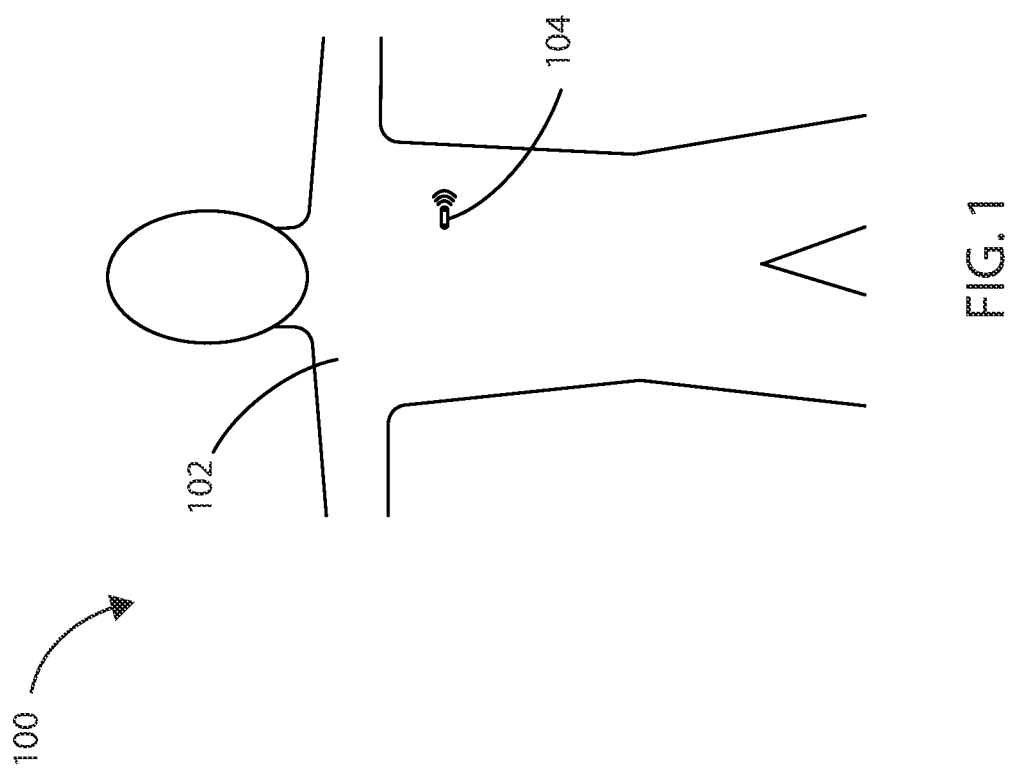
FIG. 1 is a schematic view of a subject in accordance with various embodiments herein.

In addition, systems and methods herein can be used to identify and/or diagnose disease states based on detection of irregular vibratory signals characteristic of a disease state. Without wishing to be bound by theory, it is believed that vibratory signals of various body systems can assume patterns in a disease state that are distinguishable from a healthy state allowing for disease states to be identified by analysis of body vibrations. Referring now to FIG. 1, a schematic view of a subject 100 is shown in accordance with various embodiments herein. FIG. 1 shows a subject's body 102 and an implantable monitor device 104. As used herein, the term "implantable monitor device" and "implantable monitoring device" are used synonymously.

The specific placement of the implantable monitoring device 104 in or on the subject's body 102 can substantially impact the quality of vibration signals perceptible by the implantable monitoring device 104. For example, differences in a subject's anatomy, bone density, fat distribution, organ size, and the like can affect the transmission of vibratory signals, and that detection of the vibratory signals will vary at different locations on the surface of a subject's body.

Referring now to FIG. 2, a schematic view illustrating different degrees of vibration at different positions is shown in accordance with various embodiments herein. FIG. 2 shows a subject's body 102 and implantable monitor device 104 at five different positions across the subject's torso. The implantable monitor device 104 is shown oriented at position one 200, at position two 202, at position three 204, at position four 206, and at position five 208.

The inset chart 210 of FIG. 2 shows a plot of the sound intensity as a function of the implantable monitor device position across the same positions on the subject's torso. The data shown in chart 210 includes sound intensity plotted as the root mean square of the S1 heart sound. The S1 heart sound corresponds with the beginning of the systole phase of the heart rhythm and is created by the closure of the mitral valve and the tricuspid valve. As depicted in chart 210, it can be seen that the amplitude of the S1 RMS signal varies as a function of placement location of an implantable monitor device 104 across the torso of a patient. Additional heart sounds suitable for detection by the body vibration analysis systems described herein, include the S2, S3, and S4 heart sounds.

Figure 3:
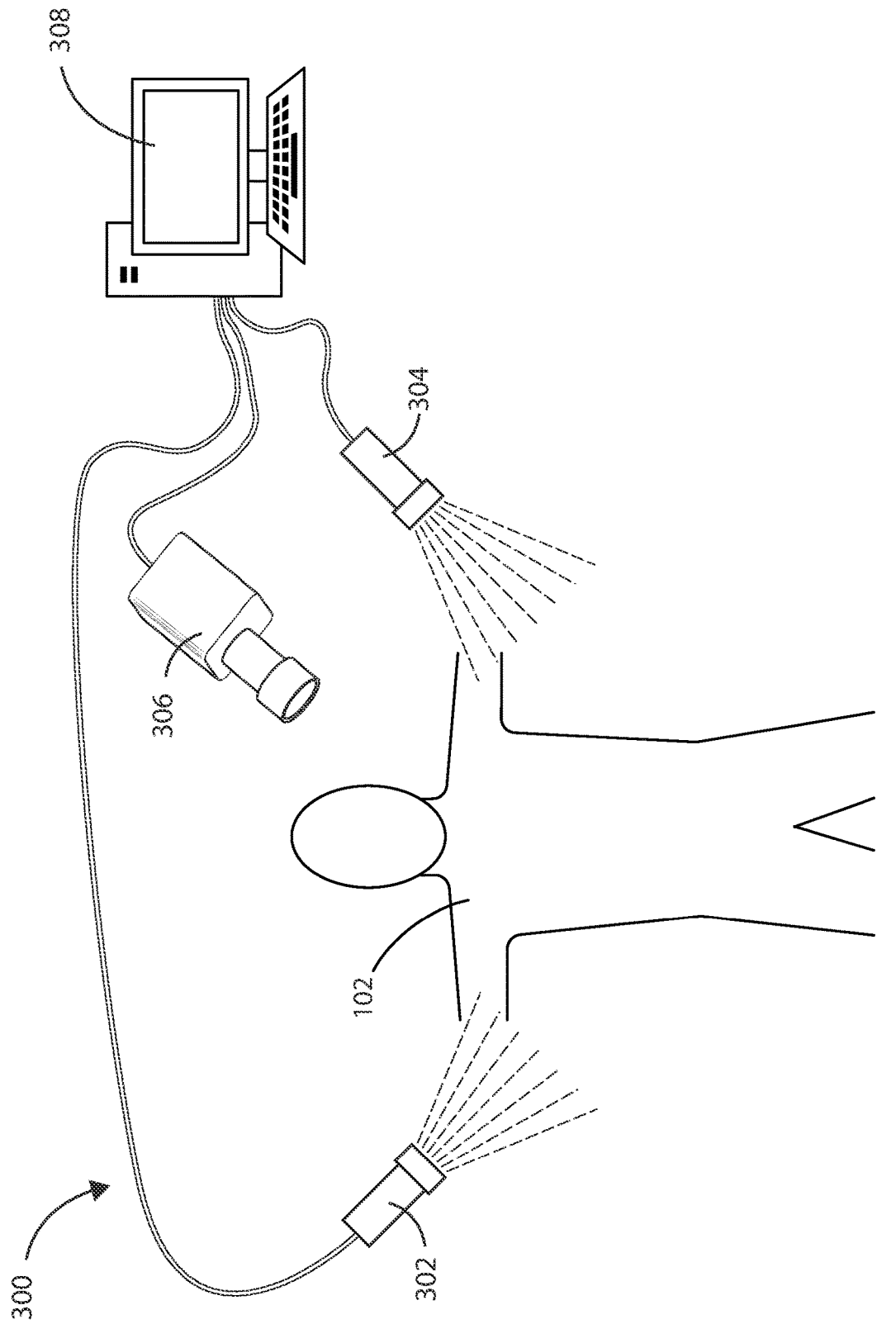
FIG. 3 is a schematic view of a system in accordance with various embodiments herein.

Body vibration analysis systems herein can detect vibratory signals on a subject's body surface and can be used to identify regions for implantation or to exclude regions of implantation. Referring now to FIG. 3, a schematic view of a system is shown in accordance with various embodiments herein. FIG. 3 shows a subject's body 102 positioned within the environment of a body vibration analysis system 300. FIG. 3 shows body vibration analysis system 300 including a first light source 302 and a second light source 304. The body vibration analysis system 300 further includes a camera 306 and a computer 308 having a control circuit (described further below). It will be appreciated that in some embodiments, the body vibration analysis system 300 can include more than one camera and/or more than one computing device.

In various embodiments, the first light source 302 can be configured to illuminate a surface of the body 102 from a first angle with a first set of lighted features (described further below). In various embodiments, the second light source 304 can be configured to illuminate a surface of the body 102 from a second angle with a second set of lighted features.

In some embodiments, at least one of the first light source 302 and second light source 304 can include any light source that can generate detectable light in the visible spectrum of from about 350 nanometers (nm) to 800 nm. However, in some embodiments, at least one of the first light source 302 and second light source 304 can include any light source that can generate camera-detectable light outside of the visible spectrum (less than 350 nanometers or greater than 800 nanometers) In yet other embodiments, at least one of the first light source 302 and the second light source 304 can have wavelengths in the infrared range (e.g., from about 700 nm to about 1 millimeter (mm)) or the ultraviolet range (e.g., from about 10 nm to about 400 nm).

It will be appreciated that in some embodiments, the first light source 302 and the second light source 304 can have the same wavelength (band or peak wavelength). In other embodiments, the first light source 302 and the second light source 304 can have the different wavelengths (band or beak wavelength).

In some embodiments, light sources herein can include a laser light source. However, in some embodiments, light sources herein can include, but are not limited to, incandescent lights, LED lights, fluorescent lights, halogen lights, tungsten-halogen lights, high-intensity discharge lights, mercury-halide lights, and the like.

In various embodiments, the first angle of incident light generated by the first light source and the second angle of incident light generated by the second light source can intersect at an angle of about 10 to 45 degrees. In some embodiments, the first angle and the second angle can intersect at an angle of from greater than or equal to 5 degrees, 10 degrees, 15 degrees, 20 degrees, 25 degrees, 30 degrees, 35 degrees, 40 degrees, 45 degrees, 50 degrees, 55 degrees, or 60 degrees, or can be an amount falling within a range between any of the foregoing.

The camera 306 of the body vibration analysis system 300 can be configured to detect light reflected from the surface of the body 102. In various embodiments, the camera is a color camera. In other embodiments, the camera is a black and white camera. In various embodiments, the camera 306 can be configured to detect light reflected from the bare skin surface of the body 102. In other embodiments, the camera 306 can be configured to detect light reflected from markers, clothing, blankets, or other items disposed over the bare skin surface of the body 102.

The computer 308, including control circuit (described further below) can be configured to receive one or more inputs from the camera 306 and can determine spatial vibration as a function of location on the surface of the body 102. It will be appreciated that the computer 308 can be configured to independently track movement of each of the lighted features within the sets of lighted features relative to a starting position of each of the lighted features.

It will be appreciated that various other pieces of equipment for body surface analysis are also contemplated herein. For example, in some embodiments, a digital image correlation type body surface analysis system can be included and a control circuit can be configured to receive input from the body analysis system including spatial vibration as a function of location on the surface of the body and perform various functions such as calculating a location for implanting a medical device based on the spatial vibration as a function of location on the surface of the body. In some cases, such digital image correlation type systems can include two separate cameras at two separate positions. The data generated by the two separate cameras can then be correlated in order to derived information regarding the body surface including vibration thereof. Digital image correlation is an optical technique used to measure deformation on an object surface. In some cases, the technique tracks the gray value pattern in small neighborhoods called subsets during deformation. Some aspects of digital image correlation system are described in U.S. Published Appl. No. 2017/0281009, the content of which is herein incorporated by reference.

Figure 4:
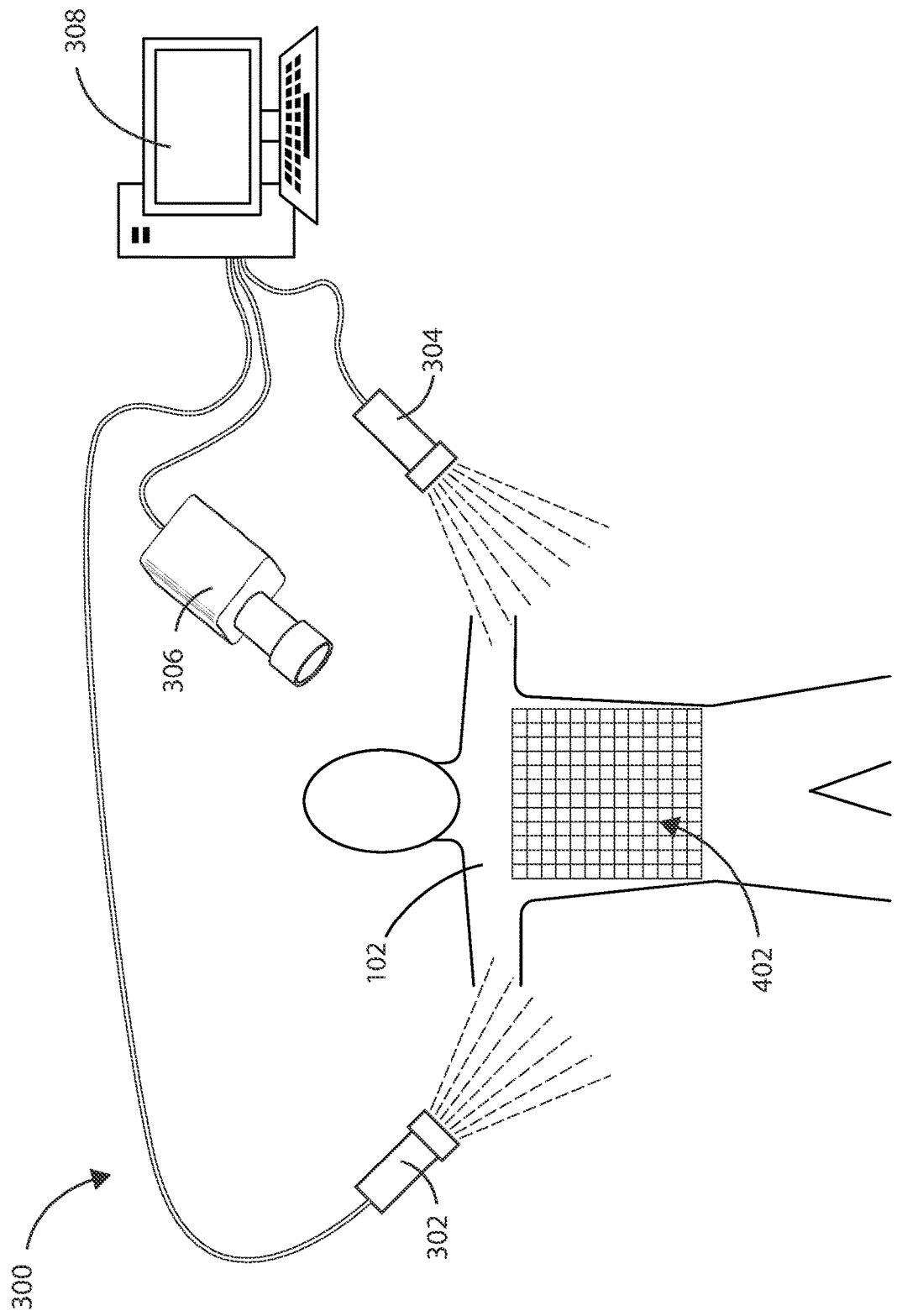
FIG. 4 is a schematic view of a system in accordance with various embodiments herein.

The body vibration analysis system 300 can be used to generate a body surface map corresponding to a surface of a subject's body. Referring now to FIG. 4, a schematic view of a system is shown in accordance with various embodiments herein. FIG. 4 shows the body vibration analysis system 300 as described with respect to FIG. 3, where a subject's body 102 positioned within the environment of a body vibration analysis system 300, and includes a body surface map 402 corresponding to a surface of the subject's body. The control circuit of computer 308 can be configured to generate the body surface map as a function of determined spatial vibration. In various embodiments, the control circuit can be further configured to calculate a location for sensing vibrations within a particular frequency range based on the determined spatial vibration as a function of location on the surface of the body.

The body surface map 402 can illustrate one or more parameters as a function of spatial location. For example, the body surface map 402 can illustrate determined movement/vibration (in absolute terms or relative terms-such as relative to other locations within the body surface map), frequencies of movement/vibration, and the like.

The body surface map 402 can correspond to any surface of the subject's body. In some embodiments, the body surface map 402 can correspond to an anterior surface of a subject's body. In other embodiments, the body surface map 402 can correspond to a posterior surface of a subject's body. In some embodiments, the body surface map 402 can correspond a region of the body such as the torso. In some embodiments, the body surface map can correspond a region of the body such as the abdomen or chest. It will be appreciated that the body surface map 402 can be generated by the computer 308 and displayed on a monitor such as a computer monitor. In some embodiments, the body surface map 402 can be generated within the computer 308 and projected onto the surface of the subject's body so as to further assist with identifying implantable monitor device location on the surface of the subject's body.

In various embodiments, the body surface map can be correlated with other data detected by additional measuring devices, including but not to be limited to one or more of electrocardiogram sensors, pulse oximeter sensors, photoplethysmographic (PPG) sensors, breath monitors, and the like. The body surface maps herein can thus be aligned to one or more physiological vibration cycles detected within one or more of the locations within the body as described below.

In various embodiments, the body surface map can be compared against a template body surface map generated by averaging the body surface map of a population of other individuals of similar body size and shape. In various embodiments, the systems herein can include multiple template body surface maps for multiple populations of individuals with a similar body size and shape. It will be further appreciated that each body surface map generated herein is unique to each individual and can provide precise localization for implantation of an implantable monitor device.

In various embodiments, the control circuit can be further be configured to average spatial vibration as a function of location on the surface of the body over a plurality of physiological vibration cycles. In some embodiments, the physiological vibration cycles can include at least one of cardiac cycles and pulmonary cycles. In other embodiments, the physiological vibration cycles can include gastrointestinal signals and/or other physiological signals or cycles. The physiological vibration cycles can originate from various structures and locations within the cardiovascular, pulmonary, or gastrointestinal systems, or other systems of the body. Some exemplary cardiovascular components/structures that can be the origin of physiological vibration cycles can include the mitral valve, the tricuspid valve, the aortic valve, the pulmonary valve, the aorta, the vena cava, and turbulent blood flow within any chamber of the heart. Some exemplary pulmonary components that can be the origin of physiological vibration cycles can include those originating in the major and minor structure of the lung, including the alveoli, the bronchial tree, the trachea, and the pleura. Some exemplary gastrointestinal components that can be the origin of physiological vibration cycles can include the esophagus, the stomach, the duodenum, the jejunum, the ileum, the colon, the pancreas, the gallbladder, and the liver.

In some embodiments, the control circuit can be configured to diagnose a disease state based on the determined spatial vibration as a function of location on the surface of the body. Various disease states can produce one or more vibratory signals that include irregular vibration patterns when compared to a healthy state. Various disease states can include disease states of the cardiovascular, pulmonary, and gastrointestinal systems. Exemplary cardiovascular disease states/symptoms can include elevated left-sided filling pressures, abdominal aortic aneurism, vascular stenosis, arteriosclerosis, heart valve prolapse, heart valve stenosis, atrial fibrillation, cardiac hypertrophy, and the like. Exemplary pulmonary disease states/symptoms can include asthma, chronic obstructive pulmonary disease, pulmonary hypertension, tuberculosis, and the like. Exemplary gastrointestinal disease states can include intestinal obstruction of the small or large intestine, delayed gastric emptying, gastroesophageal reflux, common bile duct obstruction, and the like.

In various embodiments, the body vibration analysis system 300 further can include one or more sensors, where the control circuit can be further configured to use a signal from the sensor(s) to separate and align spatial vibration data representing different physiological vibration cycles. In various embodiments, the sensor can include an electrocardiogram (i.e., EKG or ECG) sensor. In other embodiments, the sensor can include an acoustic sensor configured to detect lung sounds, such as for example breath sounds, or bowel sounds, such as for example peristalsis.

Figure 5:
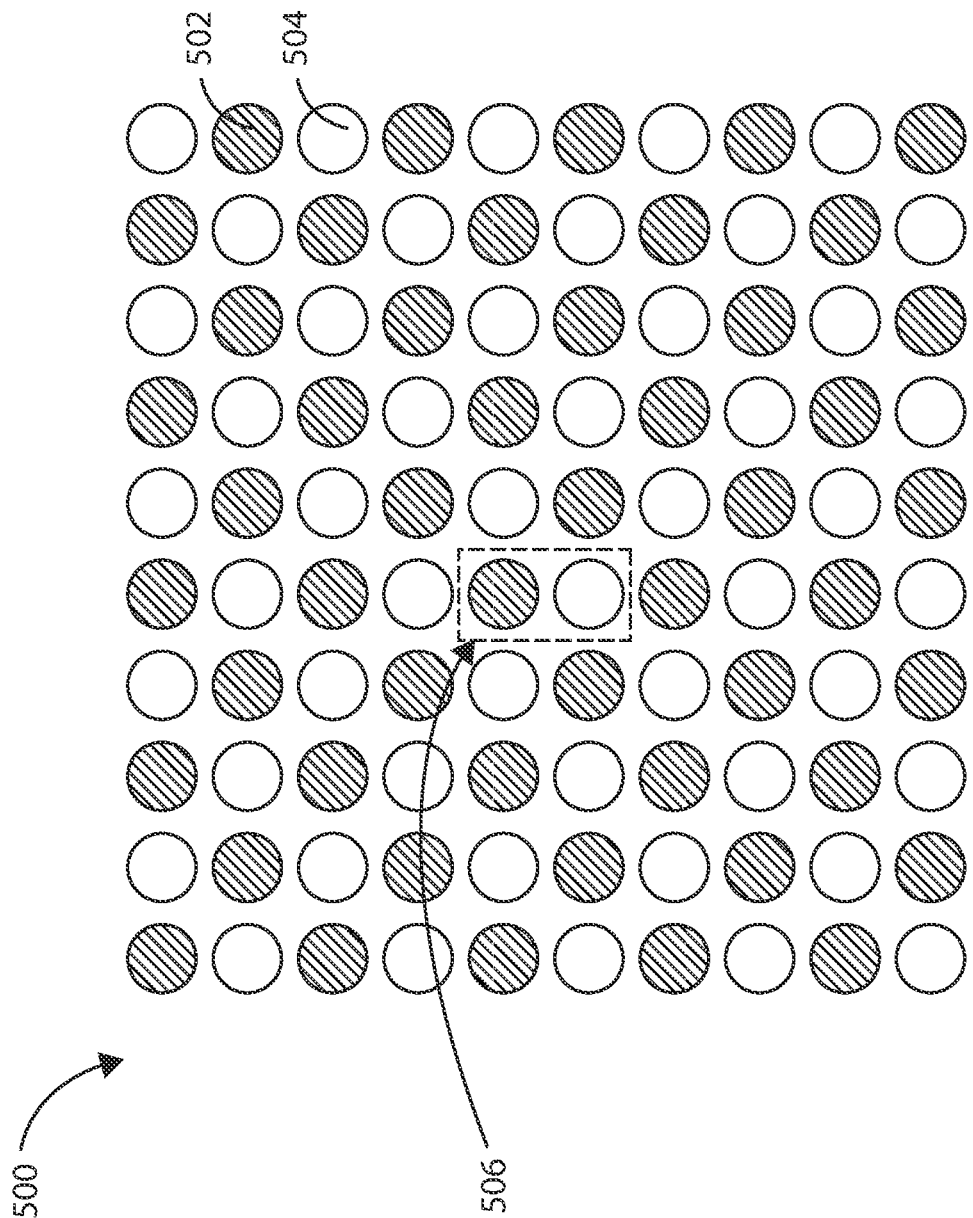
FIG. 5 is a schematic view of two sets of lighted features in accordance with various embodiments herein.

The body vibration analysis system 300 can generate a body surface map corresponding to a surface of a subject's body through use of a vibrational mapping using at least two different sets of lighted features (described further below). Referring now to FIG. 5, a schematic view of two sets of lighted features is shown in accordance with various embodiments herein. The body vibration analysis systems described herein can project an array of lighted features 500 onto the surface of a subject's body in order to generate the body surface map 402 as shown in FIG. 4. The array of lighted features 500 includes a first set of lighted features 502 and a second set of lighted features 504.

Each lighted feature within the array of lighted features 500 can move independently in response to vibratory signals experienced at various locations within the array on the surface of the subject's body. A camera (not shown in FIG. 5) can independently track the movement of each lighted features within the array and the computer 308 and control circuit can be configured to receive one or more inputs from the camera and determine spatial vibration as a function of location on the surface of the body. The array of lighted features 500 as shown in FIG. 5 includes a pair of lighted features 506, which includes a first lighted feature 502 from the first set of lighted features and a second lighted feature 504 from the second set of lighted features. For the purpose of illustration of movement, the pair of lighted features 506 is discussed in further detail in reference to FIG. 6.

Figure 6:
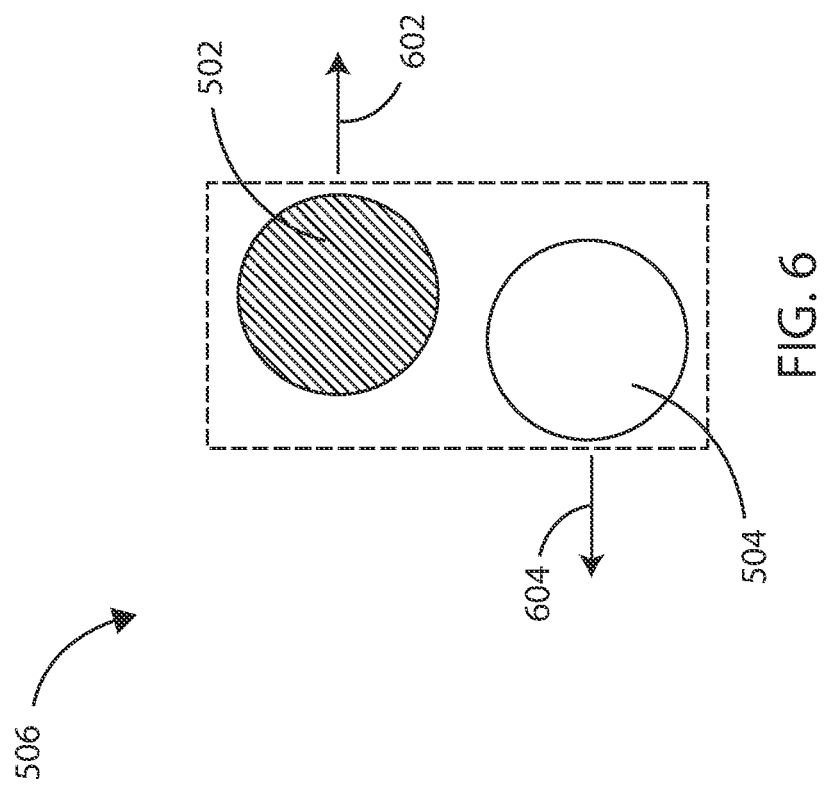
FIG. 6 is a schematic view illustrating movement of lighted features in accordance with various embodiments herein.

Referring now to FIG. 6, a schematic view illustrating movement of lighted features is shown in accordance with various embodiments herein. The pair of lighted features 506 includes a first lighted feature 502 from the first set of lighted features and a second lighted feature 504 from the second set of lighted features. While the pair of lighted features as shown in FIG. 6 illustrates movement of just the pair of lighted features 506, it will be appreciated that in practice the lighted features within an array of lighted features, such as array of lighted features 500 in FIG. 5, can each experience a degree of independent movement in response to the vibratory signals as described herein. It will be appreciated that in some locations on the surface of a subject's body, one or more lighted features might not experience measurable movement.

Movement of each lighted feature within an array of lighted features can occur in many different directions in response to how each lighted feature experiences a vibratory signal from the subject's body. In some embodiments, one or more of the lighted features within the array can be displaced in a first displacement direction 602 relative to a starting position. In other embodiments, one or more of the lighted features can be displaced in a second displacement direction 604 relative to a starting position. In reference to FIG. 6, first lighted feature 502 can be displaced in response to a vibratory signal in a first displacement direction 602, while second lighted feature 504 can be displaced in response to a vibratory signal in a second displacement direction 604. In some embodiments, both the first lighted feature 502 and the second lighted feature 504 can be displaced in response to a vibratory signal in a first displacement direction 602. In other embodiments, both the first lighted feature 502 and the second lighted feature 504 can be displaced in response to a vibratory signal in a second displacement direction 604. In some embodiments, the magnitude of displacement of a lighted feature can be used by the system to derive the magnitude of movement/vibration at the site of the lighted feature. In some embodiments, the magnitude of relative displacement of one light feature compared to a second lighted feature (e.g., relative movement between a pair) can be used by the system to derive the magnitude of movement/vibration at the site of the lighted feature pair.

Each lighted feature within an array can be displaced a distance from a starting position to a displaced position in any direction (as dependent on both the angle from which the light feature is projected and the movement of the surface of the body) about a center point through the lighted feature including from about 0 degrees to 360 degrees. In some embodiments, the displacement of the lighted feature can occur in a direction about a center point through the lighted feature that is equal to 0 degrees, 5 degrees, 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees, 190 degrees, 200 degrees, 210 degrees, 220 degrees, 230 degrees, 240 degrees, 250 degrees, 260 degrees, 270 degrees, 280 degrees, 290 degrees, 300 degrees, 310 degrees, 320 degrees, 330 degrees, 340 degrees, 350 degrees, or 360 degrees, or can be an amount falling within a range between any of the foregoing.

The displacement distance between the starting position of each of the lighted features to a displaced position of each of the lighted features can include displacement distances ranging from about 50 nm to about 1 centimeter (cm). In some embodiments, the distance between the starting position of each of the lighted features to a displaced position of each of the lighted features described herein can be greater than or equal to 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 1 µm, 10 µm, 20 µm, 30 µm, 40 µm, 50 µm, 60 µm, 70 µm, 80 µm, 90 µm, 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 1 mm, 10 mm, 20 mm, 30 mm, 40 mm, 50 mm, 60 mm, 70 mm, 80 mm, 90 mm, 100 mm, 125 mm, 150 mm, 175 mm, 200 mm, 225 mm, 250 mm, 275 mm, 300 mm, 325 mm, 350 mm, 375 mm, 400 mm, 425 mm, 450 mm, 475 mm, 500 mm, 525 mm, 550 mm, 575 mm, 600 mm, 625 mm, 650 mm, 675 mm, 700 mm, 725 mm, 750 mm, 775 mm, 800 mm, 825 mm, 850 mm, 875 mm, 900 mm, 1 cm, 2 cm, or 3 cm, or can be an amount falling within a range between any of the foregoing.

The resolution of detection of a displacement distance for each lighted feature by the cameras in the systems herein can include a resolution falling within a range of about 1 nm to about 5 cm or more. In various embodiments, the resolution of detection of a displacement distance for each lighted feature by the cameras in the systems herein can include a resolution greater than or equal to 1 nm, 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 1 µm, 10 µm, 20 µm, 30 µm, 40 µm, 50 µm, 60 µm, 70 µm, 80 µm, 90 µm, or 100 µm, 500 µm, 1 mm, 2 mm, 3 mm, 4 mm, 5 mm, 7.5 mm, 1 cm, 2 cm, 3 cm, 4 cm, 5 cm, or 10 cm, or can be an amount falling within a range between any of the foregoing.

Figure 7:
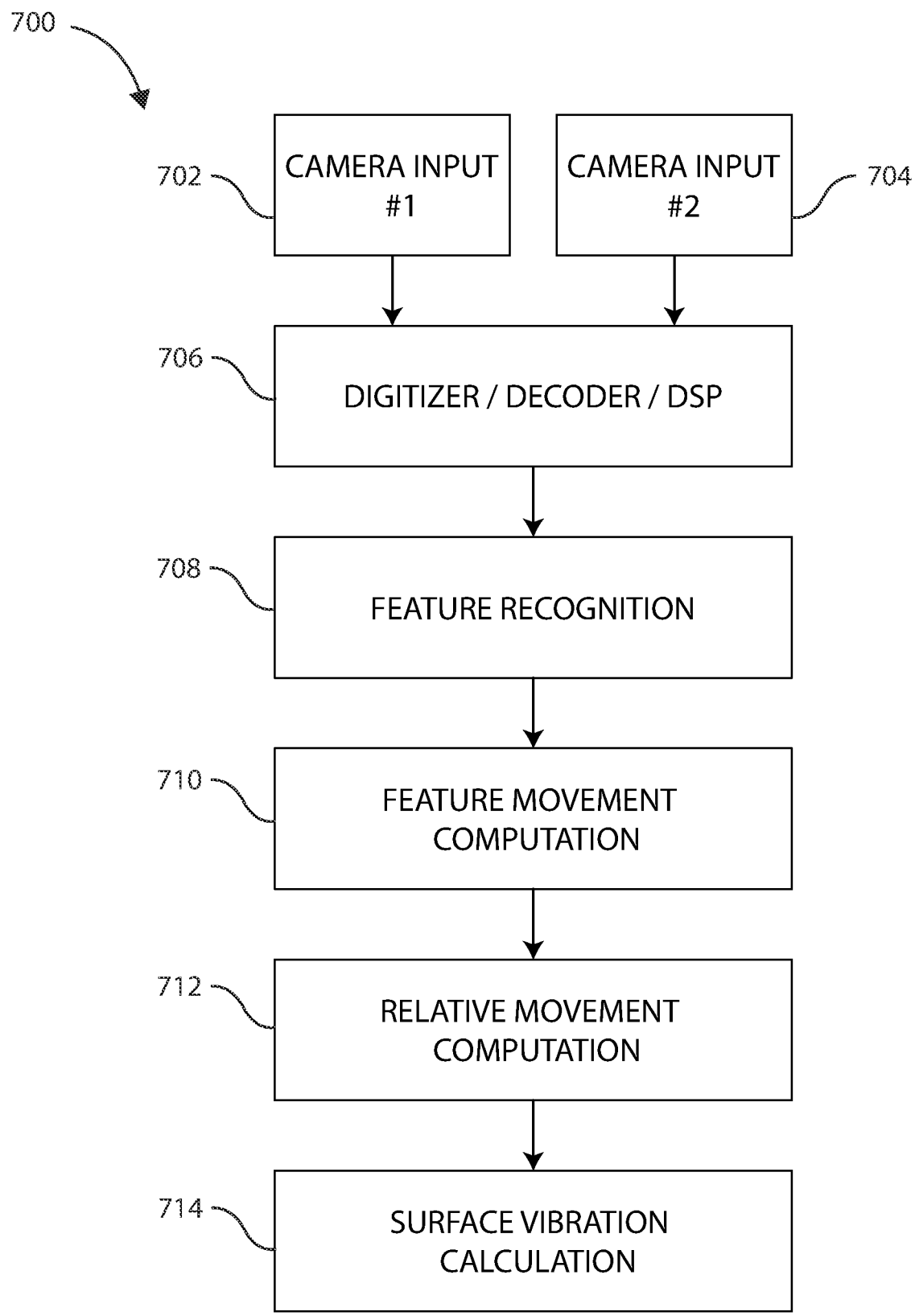
FIG. 7 is a block diagram of operations in accordance with various embodiments herein.

Referring now to FIG. 7, a block diagram 700 of operations is shown in accordance with various embodiments herein. The operations of the body vibration analysis systems described herein can begin with the camera detecting light reflected from the surface of a subject's body and generating an analog or a digital video signal via camera input #1 at 702 and camera input #2 at 704. In some embodiments, the video signal can be digitized and/or decoded by a digitizer/decoder/digital signal processor (DSP) at 706. Various filtering (digital or analog) and/or processing operations can be conducted by the digitizer/decoder/DSP. In some embodiments, light that is not associated with lighted features can be filtered out. In some embodiments, the digitizer/decoder/DSP can generate one or more spatio-temporal data signals corresponding to the digitized/decoded input signal that can be used synchronize multiple digitized/decoded data signals to one another.

It will be appreciated that video signal data can be collected for any amount of time from about 30 seconds to up to 60 minutes. In various embodiments, analog video signal data can be collected for more than 60 minutes. In various embodiments, analog video signal data can be collected for less than 30 seconds. In some embodiments, the analog video signal data can be collected for greater than or equal to 10 seconds (sec), 20 sec, 30 sec, 40 sec, 50 sec, 1 minute (min), 10 min, 20 min, 30 min, 40 min, 50 min, 1 hour (hr), 2 hr, or 3 hr, or can be an amount falling within a range between any of the foregoing.

In some embodiments, the digitizer/decoder/DSP can pass signals/data to a feature recognition module 708 that can be configured to recognize one or more characteristics of the lighted features, including the colors, shapes, sizes, and light intensities of the various lighted features as projected on the surface of a subject's body. In some embodiments, features can be identified starting with the application of an edge recognition algorithm. The feature recognition module 708 can be further configured to recognize one or more positions and/or coordinates of the lighted features during the course of evaluating body vibrations in response to a vibratory signal originating within a subject's body. The feature recognition module 708 can be configured to differentiate between the various colors, sizes, shapes, and light intensities and can assign positional information to each of the lighted features within one or more sets of lighted features. In various embodiments, the feature recognition module 708 can generate positional information, such as regions of pixels, within the signals/data that correspond to the positions of the lighted features on various regions on the surface of a subject's body.

Feature recognition techniques/algorithms used by the feature recognition module can include, but are not limited to, Canny, Sobel, Kayyali, Plessey, SUSAN, Shi & Tomasi, Level curve curvature, Lapacian of Gaussian, Difference of Gaussian, Determinant of Hessian, MSER, PCBR, Grey-level blobs, and the like. Exemplary feature recognition techniques are described in U.S. Pat. Nos. 5,768,421; 7,343,278; and 9,269,022; and U.S. Publ. Appl. Nos. 2006/0045337; and 2017/0286809, the content of which related to feature recognition techniques is herein incorporated by reference.

The feature recognition module 708 can pass signals/data and/or positional information about the lighted features along to the feature movement computation module 710. The feature movement computation module 710 can further process the signals/data and/or positional information to extract feature movement information corresponding to displacement of the lighted features in response to vibratory signals. The feature movement information can be used to further elucidate regions on the surface of the body of a subject that experience an increased amount of vibration relative to other locations on the surface of the body of the subject. The signals/data and/or positional information can be passed along with the feature movement information to the relative movement computation module 712.

The relative movement computation module 712 can further process the digitized/decoded data signal, positional information, and the feature movement information, and can compare any given lighted features from a starting position at any given time to an ending position in response to one or more vibratory signals to generate relative movement information. The relative movement information can include any information about movement of any of the lighted features with respect to an initial time (t=0 seconds) or to any given time during the course of data acquisition. The signals/data, positional information, feature movement information, and relative movement information can then be passed on to a signal vibration calculation module 714 where the body surface map can be generated specifically to a given subject's signatory vibration signals.

Figure 8:
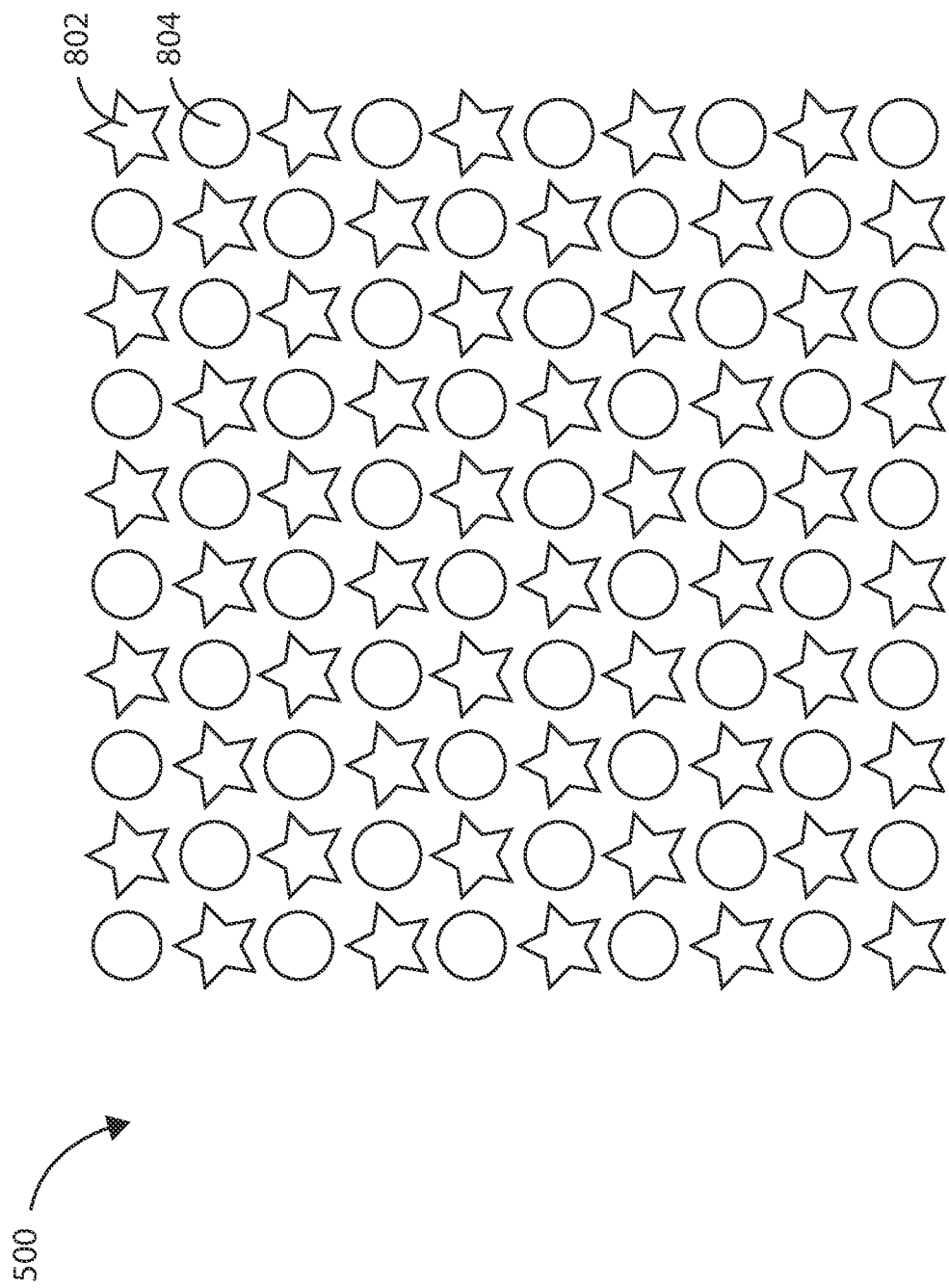
FIG. 8 is a schematic view of two sets of lighted features in accordance with various embodiments herein.

In some embodiments, the two sets of light features need not be different colors to be distinguished from one another. For example, in some embodiments, two sets of lighted features having different shapes but the same color can be used in the body vibration analysis systems described herein. Referring now to FIG. 8, a schematic view of two sets of lighted features is shown in accordance with various embodiments herein. The two sets of lighted features creates an array of lighted features 500 that includes a first lighted feature shape 802 and a second lighted feature shape 804. While the first lighted feature shape 802 is that of a star and the second lighted feature shape 804 is that of a circle, it will be appreciated that any shape can be used for the first and second lighted feature shapes, as described elsewhere herein. While are depicted as being the same color, it is possible that the first lighted feature shape 802 and second lighted feature shape 804 can be a different color.

Figure 9:
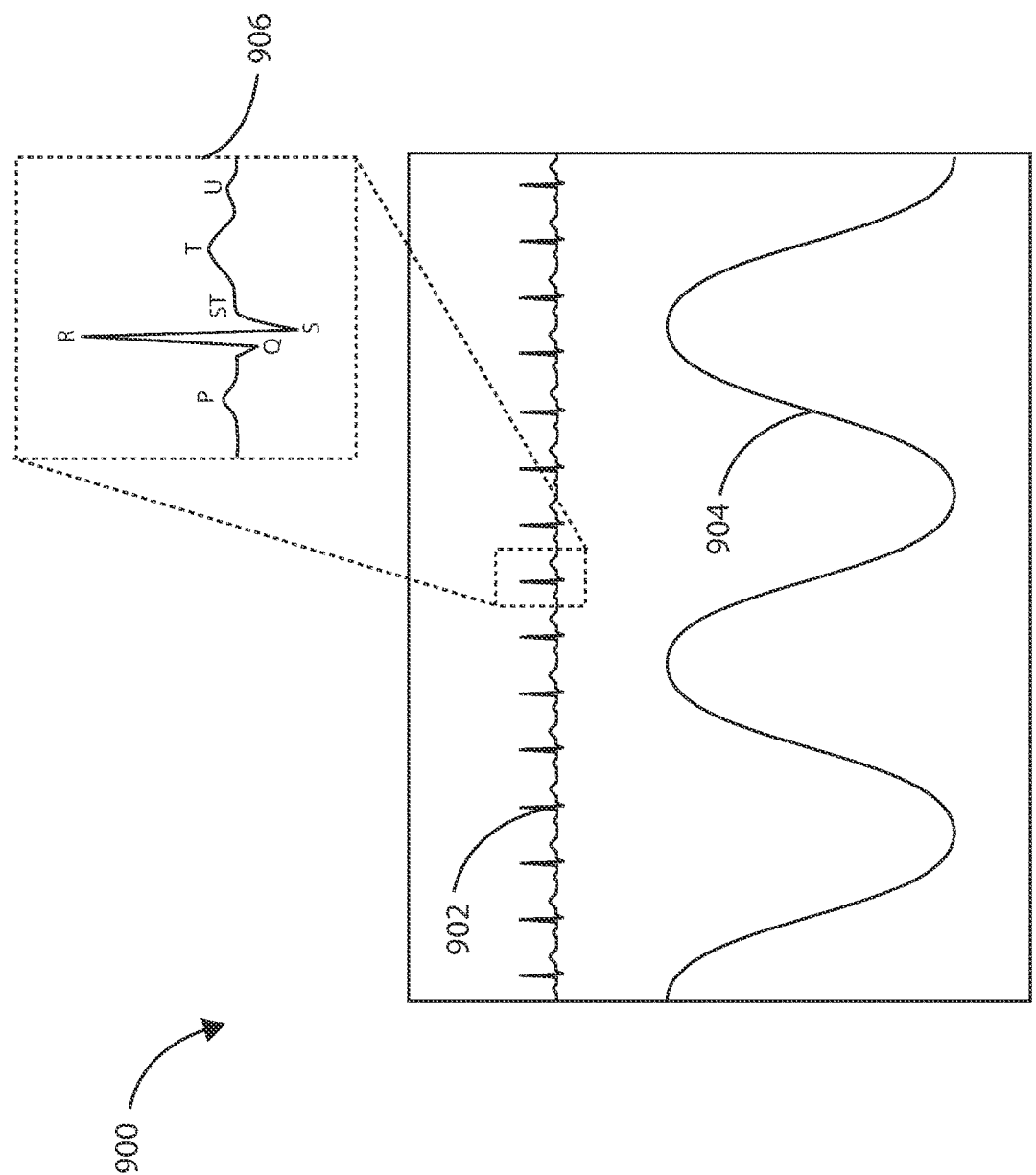
FIG. 9 is a schematic view of signals representing physiological cycles in accordance with various embodiments herein.

The body vibration analysis systems herein can be configured to detect and analyze vibration as a function of location on the surface of a subject's body over a plurality of physiological vibration cycles to generate a body surface map as described herein. Referring now to FIG. 9, a schematic view of signals representing physiological cycles is shown in accordance with various embodiments herein. The body vibration analysis system can be configured to create one or more graphs of physiological vibration cycles 900. The plurality of physiological vibration cycles 900 can include cardiac cycles 902 and pulmonary cycles 904. In some embodiments, the physiological vibration cycles can include one or more plots of gastrointestinal cycles (not shown).

The cardiac cycles 902 can include cover the span of one or more PQRST electrocardiogram (i.e., EKG or ECG) waveforms 906. PQRST waveform 906 includes the P-wave, the QRS complex, the T-wave, the ST segment, and the U-wave plotted as function of time. An exemplary pulmonary cycle 904 includes a plot of the respiration by the lungs over time. The amplitude(s) of the physiological vibration cycles 900, such as the peaks of the PQRST EKG waveform 906, can be measured and can be averaged over a predetermined time interval and can be aligned with the body surface map as described herein.

In various embodiments, the control circuit (described further below) can be further configured to average spatial vibration as a function of location on the surface of the body over a plurality of physiological vibration cycles 900. For example, time synchronous data from a sensor (such as an EKG or ECG signal in the case of a cardiac cycle) can be used to break up vibration data into segments representing a full cardiac cycle (such as R to R, P to P, or the like). Then the separated segments can be aligned based on the EKG or ECG data features and vibration data can then be averaged over a plurality of physiological cycles. In this way, a vibration map can be created that represents not just one physiological cycle of interest but the average vibration happening over a plurality of physiological cycles.

In various embodiments, the physiological signals can be filtered and a signature thereof identified. In various embodiments, the control circuit (described further below) can be further configured to calculate a location for sensing vibrations within a particular frequency range based on the determined spatial vibration as a function of location on the surface of the body. In various embodiments, the vibration data representing any one of the physiological signals can be filtered using a high pass filter, a low pass filter, or a band pass filter to focus on a physiological signal of interest.

Figure 10:
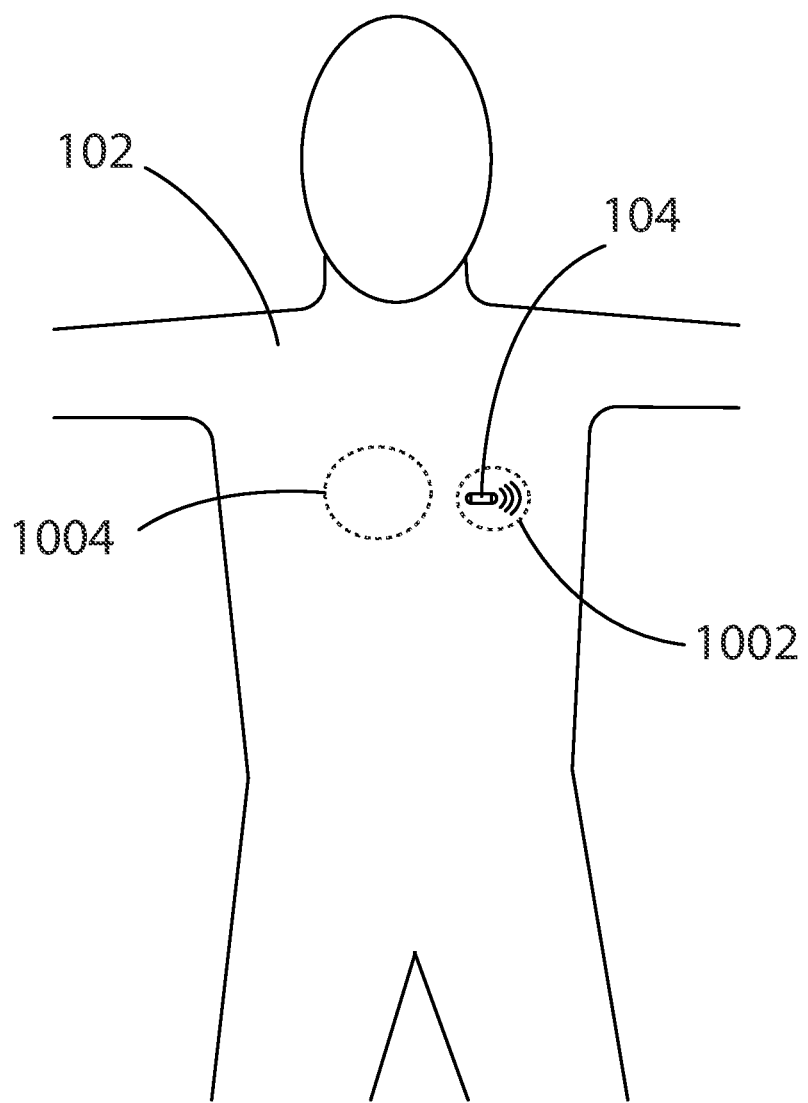
FIG. 10 is a schematic view of locations for sensing vibrations within a particular frequency range in accordance with various embodiments herein.

The physiological vibration cycles can be quantified within the body surface maps and a location for implantation of an implantable sensor device can be identified. Referring now to FIG. 10, a schematic view of locations for sensing vibrations within a particular frequency range is shown in accordance with various embodiments herein. FIG. 10 shows a subject's body 102 and an implantable monitor device 104. Exemplary implant positions are identified on the subject's body 102, including a first implant position 1002 and a second implant position 1004. For example, position 1002 may be best for sensing S1 heart sounds, but position 1004 may be best for sensing pulmonary phenomena. Thus, a clinician can be guided to the best site for implantation based on the type of monitoring device used and what physiological data they are most interested in monitoring. FIG. 10 shows the implantable monitor device 104 implanted at the first implant position 1002.

Figure 11:
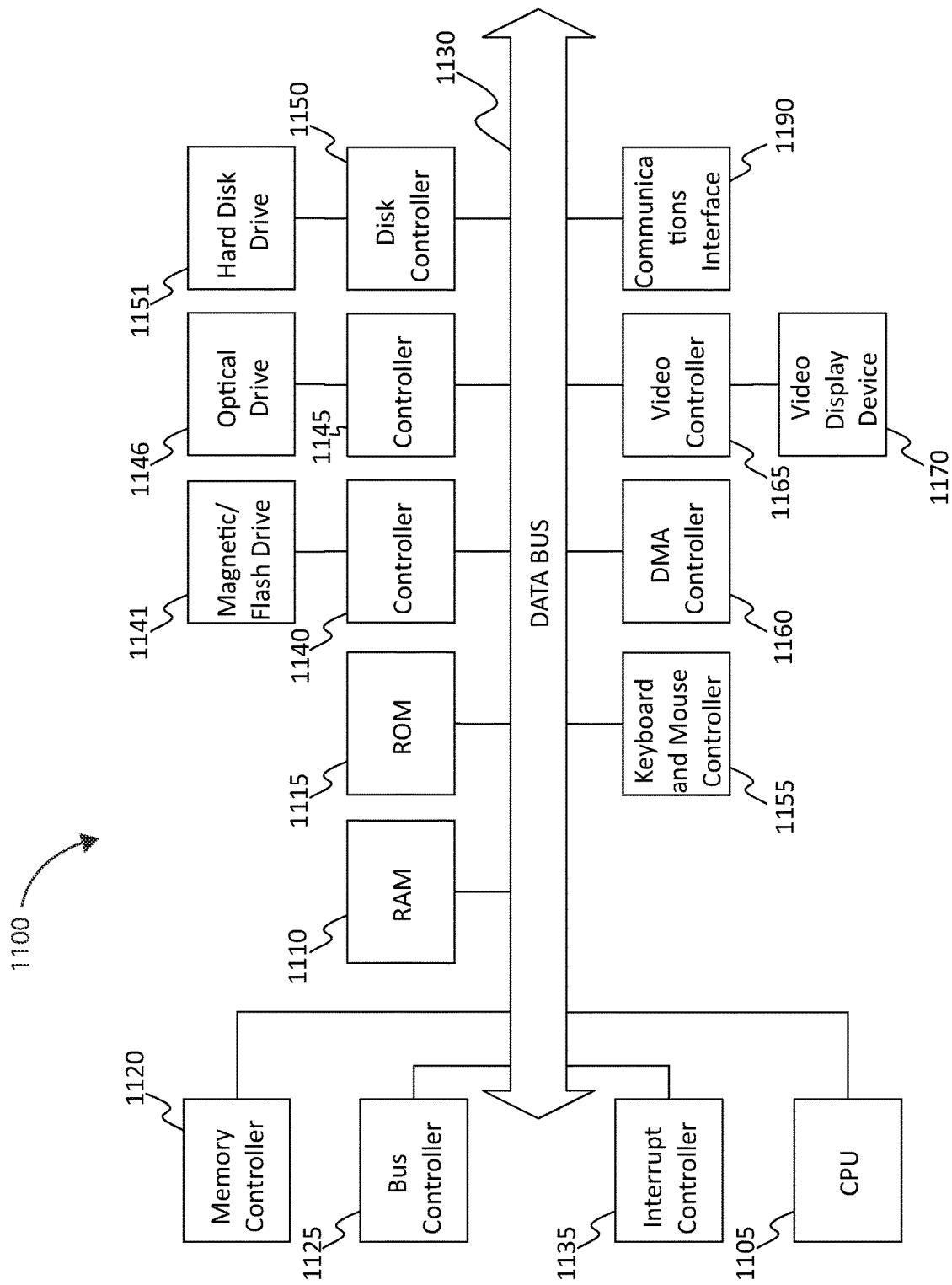
FIG. 11 is a diagram of various system components in accordance with some embodiments herein.

Referring now to FIG. 11, a diagram 1100 of various system components 1100 is shown in accordance with some embodiments herein. A computing device (not shown in this view) includes a control circuit 1105. In various embodiments, the control circuit 1105 configured to receive an input from the camera 306 and determine spatial vibration as a function of location on the surface of the body. In various embodiments, the control circuit 1105 can be further configured to generate a body surface map 402 as a function of determined spatial vibration. In various embodiments, the control circuit 1105 can be further configured to calculate a location for sensing vibrations within a particular frequency range based on the determined spatial vibration as a function of location on the surface of the body. In various embodiments, the control circuit 1105 can be further configured to diagnose a disease state based on the determined spatial vibration as a function of location on the surface of the body. In various embodiments, the control circuit 1105 can be further configured to average spatial vibration as a function of location on the surface of the body over a physiological vibration cycles. In various embodiments, the control circuit 1105 can be further configured to use a signal from the sensor to separate and align spatial vibration data representing different physiological vibration cycles.

Devices to display body maps herein can include components common to many computing devices. Referring now to FIG. 11, a diagram of various components is shown in accordance with some embodiments. The system can include a central processing circuit that can include various components such as a central processing unit. By way of example, the system can include a central processing unit (CPU) 1105 or processor, which may include a conventional microprocessor, microcontroller, FPGA device, or the like. In some embodiments the system can also include random access memory (RAM) 1110 for temporary storage of information, and read only memory (ROM) 1115 for permanent storage of information. A memory controller 1120 is provided for controlling system RAM 1110. A bus controller 1125 is provided for controlling data bus 1130, and an interrupt controller 1135 is used for receiving and processing various interrupt signals from the other system components.

Mass storage can be provided by a magnetic or flash memory drive 1141 including removable or non-removable media, which is connected to bus 1130 by controller 1140, an optical drive such as CD-ROM or DVD drive 1146, which is connected to bus 1130 by controller 1145, and/or hard disk drive 1151 (magnetic or solid state), which is connected to bus 1130 by controller 1150. In some embodiments, mass storage can be provided by a device connected through a universal serial bus (USB), eSATA, FireWire, or Thunderbolt interface or other type of connection. User input to the programmer system may be provided by a number of devices. For example, a keyboard and mouse can be connected to bus 1130 by keyboard and mouse controller 1155. DMA controller 1160 is provided for performing direct memory access to system RAM 1110. In some embodiments, user input can also be provided by a pen, light pen, glove, wearable object, gesture control interface, or the like.

A video processing circuit can be included and can generate a user interface. The video processing circuit can include a video controller 1165 or video output, which controls video display 1170. In some embodiments, the video controller 1165 can also include one or more graphical processing units (GPUs). The video processing circuit can be in communication with the central processing circuit.

The system can also include a communications interface 1190 or communications circuit which allows the system to interface and exchange data with other systems and/or servers. The communications circuit can be in communication with the central processing circuit. In some embodiments, the communications interface 1190 can include a network interface card or circuit to facilitate communication with a packet switched (such as IP) or other type of data network.

It will be appreciated that some embodiments may lack various elements illustrated in FIG. 11. In addition, the architecture shown in FIG. 11 is merely one example of how discrete components can be arranged and other architectures are explicitly contemplated herein.

In addition to, or instead of, the components described with respect to FIG. 11, it will be appreciated that the system can also include a microcontroller, a programmable logic controller (PLC), an ASIC, an FPGA, a microprocessor, or other suitable technology.

The video processing circuit (either locally or on a remote node) can generate a map image (2D or 3D) based on information including one or more of geometry, viewpoint, texture, lighting and shading information, and other information described above. In some embodiments, information for rendering an image is combined within a scene file. The term "graphics pipeline" can be used to refer to the sequence of steps used to create a 2D raster representation of a 3D scene. The video processing circuit can execute one or more steps of the graphics pipeline. The video processing circuit can also include one or more physical components used in the graphics pipeline. Using the information described above, the graphics pipeline can include one or more stages of creating a scene out of geometric primitives, modelling and transformation, camera transformation, lighting, projection transformation, clipping, scan conversion or rasterization, and texturing and fragment shading. In various embodiments, other operations can also be performed. In various embodiments, the graphics pipeline can use OpenGL, DirectX, or other protocols.

Implantable monitor devices herein can include those of various sizes and are not particularly limited. However, in some embodiments, devices herein are about 0.5 cm to about 2.0 cm in length along a short axis and about 1.0 cm to about 3.0 cm in length along a long axis. In some embodiments, the implantable monitor devices herein can include those that have a length along the short axis of greater than or equal to 0.25 cm, 0.50 cm, 0.75 cm, 1.00 cm and those that have a length along a long axis of greater than or equal to 1.00 cm, 1.25 cm, 1.50 cm, 1.75 cm, 2.00 cm., 2.25 cm, 2.50 cm, 2.75 cm, or 3.00 cm, or can be an amount falling within a range between any of the foregoing. It will be appreciated that the shape of implantable monitor devices herein are also not particularly limited. However, in some embodiments devices herein can include, but are not to be limited to, a square, a rectangle, an ovoid, a sphere, a trapezoid, and the like. In various embodiments, the shape of the implantable monitor devise herein can include those with tapered corners. The thickness of the implantable monitor devices herein can include those having a thickness of about 0.25 cm to about 1.5 cm. In some embodiments, the implantable monitor devices herein can include those that have a thickness of greater than or equal to 0.25 cm, 0.50 cm, 0.75 cm, 1.00 cm, or 1.50 cm, or can be an amount falling within a range between any of the foregoing.

Lighted Features

Various embodiments herein include the projection of lighted features onto a body surface. Further details about the lighted features are provided as follows. However, it will be appreciated that this is merely provided by way of example and that further variations are contemplated herein.

The systems and methods herein can utilize the movement of multiple sets of lighted features when projected on the surface of a subject's body to generate a body surface map for use in determining implantable monitor device placement and for diagnostic purposes. It will be appreciated that in some embodiments a first set of lighted features and a second set of lighted features can be used. In some embodiments, more than a first and second set of lighted features can be used. In some embodiments, a first, second, third, fourth, fifth, sixth, seventh, eighth, ninth, or tenth set of lighted features can be used. In yet other embodiments, more than a tenth set of lighted features can be used.

The lighted features within each set of lighted features suitable for use in the embodiments herein can include those having various colors, shapes, sizes, and light intensities. In some embodiments, a first set of lighted features are a different color than a second set of lighted features. In other embodiments, a first set of lighted features are a different shape than a second set of lighted features. In various embodiments, a first set of lighted features are a different light intensity than the second set of lighted features. In some embodiments, a second set of lighted features are optically distinguishable from a first set of lighted features.

It will be appreciated that in some embodiments, the color of each of the sets of lighted features can include those that are generated by light that falls within the visible spectrum or outside the visible spectrum, as described elsewhere herein. The colors can include various shades of white, black, brown, red, orange, yellow, green, blue, purple, indigo, and violet. In some embodiments the lighted features can be generated by ultraviolet or infrared light. It will further be appreciated that the sets of lighted features herein can be the same shape or different shapes, including but not limited to circles, stars, trapezoids, rectangles, triangles, ovals, and the like. In some embodiments, a first set of lighted features can be a different size than a second set of lighted features. In other embodiments, a first set of lighted features can be the same size as a second set of lighted features. In some embodiments, the lighted features can be discrete lighted features. In other embodiments, the lighted features can be connected by one or more connecting features.

The size of the lighted features suitable for use herein can include those ranging from about 1 millimeter in diameter to about 5 centimeters (cm) in diameter. In some embodiments, the diameter of the lighted features herein can be greater than or equal to 0.5 mm, 1 mm, 10 mm, 20 mm, 30 mm, 40 mm, 50 mm, 60 mm, 70 mm, 80 mm, 90 mm, or 100 mm, 125 mm, 150 mm, 175 mm, 200 mm, 225 mm, 250 mm, 275 mm, 300 mm, 325 mm, 350 mm, 375 mm, 400 mm, 425 mm, 450 mm, 475 mm, 500 mm, 525 mm, 550 mm, 575 mm, 600 mm, 625 mm, 650 mm, 675 mm, 700 mm, 725 mm, 750 mm, 775 mm, 800 mm, 825 mm, 850 mm, 875 mm, or 900 mm, 1 cm, 2 cm, 3 cm, 4 cm, 5 cm or can be an amount falling within a range between any of the foregoing.

The distance between each of the lighted features of a first set of lighted features and a second set of lighted features when projected on a subject's body can include distances ranging from about 1 millimeter to about 1 centimeter (cm) from one lighted feature of one set of lighted features to any neighboring lighted features of another set of lighted features. In some embodiments, the distance between each of the lighted features of a first set of lighted features and a second set of lighted features described herein can be greater than or equal to 0.5 mm, 1 mm, 10 mm, 20 mm, 30 mm, 40 mm, 50 mm, 60 mm, 70 mm, 80 mm, 90 mm, or 100 mm, 125 mm, 150 mm, 175 mm, 200 mm, 225 mm, 250 mm, 275 mm, 300 mm, 325 mm, 350 mm, 375 mm, 400 mm, 425 mm, 450 mm, 475 mm, 500 mm, 525 mm, 550 mm, 575 mm, 600 mm, 625 mm, 650 mm, 675 mm, 700 mm, 725 mm, 750 mm, 775 mm, 800 mm, 825 mm, 850 mm, 875 mm, or 900 mm, 1 cm, 2 cm, 3 cm, or can be an amount falling within a range between any of the foregoing. In some embodiments, the lighted features may be partially touching, but still distinguishable from one another.

It will be appreciated that in some embodiments, the lighted features herein can be evenly dispersed within an array on the surface of a subject's body such that there is a uniform distance between each lighted feature of two or more sets of lighted features. In other embodiments, the lighted features herein can be irregularly dispersed with respect to each lighted feature of two or more sets of lighted features within an array on the surface of a subject's body. In some embodiments, the light features can be present in a disordered random array such as a speckled pattern with varying distances between neighboring lighted features of two or more sets of lighted features.

Methods

Many different methods are contemplated herein, including, but not limited to, methods of making, methods of using, and the like. Aspects of system/device operation described elsewhere herein can be performed as operations of one or more methods in accordance with various embodiments herein.

Figure 12:
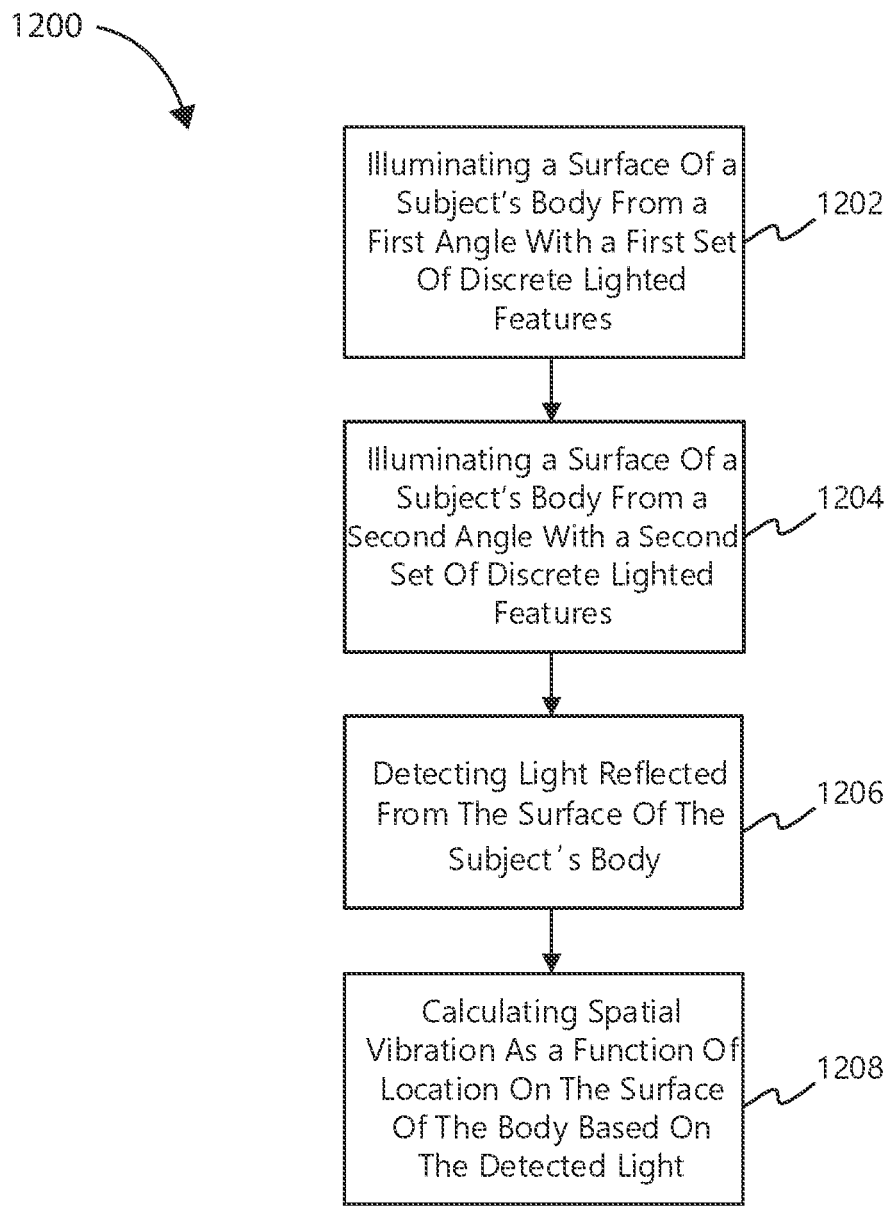
FIG. 12 is a flow diagram of a method in accordance with various embodiments herein.

Referring now to FIG. 12, a flow diagram of a method in accordance with various embodiments herein is shown. For example, in an embodiment, a method 1200 of evaluating body vibrations is included. The method 1200 includes illuminating a surface of a subject's body from a first angle with a first set of lighted features at 1202. The method 1200 can also include illuminating a surface of a subject's body from a second angle with a second set of lighted features at 1204. The method 1200 can also include detecting light reflected from the surface of the subject's body at 1206. The method 1200 can also include calculating spatial vibration as a function of location on the surface of the body based on the detected light at 1208.

In an embodiment of the method, the first set of lighted features are a different color than the second set of lighted features. In an embodiment of the method, the first set of lighted features are a different shape than the second set of lighted features. In an embodiment of the method, the first set of lighted features are a different intensity than the second set of lighted features. In an embodiment of the method, the first angle and the second angle intersect at an angle of about 10 to 45 degrees.

In an embodiment, the method can further include generating a body surface map as a function of determined spatial vibration. In an embodiment, the method can further include calculating a location for sensing vibrations within a particular frequency range based on the determined spatial vibration as a function of location on the surface of the body. In an embodiment, the method can further include diagnosing a disease state based on the determined spatial vibration as a function of location on the surface of the body. In an embodiment, the method can further include averaging spatial vibration as a function of location on the surface of the body over a plurality of physiological vibration cycles.

In an embodiment, the physiological vibration cycles can include at least one of cardiac cycles and pulmonary cycles. In an embodiment, the method can further include using a signal from a sensor to separate and align spatial vibration data representing different physiological vibration cycles. In an embodiment, the sensor can include an ECG sensor.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A human body vibration analysis system comprising:
   a first light source configured to illuminate a surface of the human body from a first angle, wherein the first light source generates a first set of lighted features, wherein the first set of lighted features comprise a first shape;
   a second light source configured to illuminate a surface of the human body from a second angle, the second angle different than the first angle, wherein the second light source generates a second set of lighted features, wherein the second set of lighted features comprise a second shape distinguishable from the first shape of the first set of lighted features;
   a camera configured to detect light reflected from the surface of the human body; and
   a control circuit configured to receive an input from the camera and assess spatial vibration as a function of location on the surface of the human body;
   wherein each of the one or more of the lighted features within the first set of lighted features and the second set of lighted features can be displaced in any direction a distance from a starting position to a displaced position on the human body in response to a vibratory signal from the human body.

2. The human body vibration analysis system of claim 1, wherein the first set of lighted features are at least one of a different color than the second set of lighted features or a different intensity than the second set of lighted features.

3. The human body vibration analysis system of claim 1, wherein the control circuit is further configured to generate a body surface map as a function of determined spatial vibration.

4. The human body vibration analysis system of claim 1, wherein the first angle and the second angle intersect at an angle of about 10 to 45 degrees.

5. The human body vibration analysis system of claim 1, wherein the control circuit is further configured to calculate a location for sensing vibrations within a particular frequency range based on the determined spatial vibration as a function of location on the surface of the human body.

6. The human body vibration analysis system of claim 1, wherein the control circuit is further configured to calculate a location for implanting a medical device based on the determined spatial vibration as a function of location on the surface of the human body.

7. The human body vibration analysis system of claim 1, wherein the control circuit is further configured to diagnose a disease state based on the determined spatial vibration as a function of location on the surface of the human body.

8. The human body vibration analysis system of claim 1, wherein the control circuit is further configured to average spatial vibration as a function of location on the surface of the human body over a plurality of physiological vibration cycles.

9. The human body vibration analysis system of claim 8, the physiological vibration cycles comprising at least one of cardiac cycles and pulmonary cycles.

10. The human body vibration analysis system of claim 1, further comprising a sensor, wherein the control circuit is further configured to use a signal from the sensor to separate and align spatial vibration data representing different physiological vibration cycles.

11. The human body vibration analysis system of claim 10, the sensor comprising an ECG sensor.

12. An implant location calculating system comprising:
    a digital image correlation subject body surface analysis system comprising:
       a first light source configured to illuminate the surface of the subject's body from a first angle, wherein the first light source generates a first set of lighted features, wherein the first set of lighted features comprise a first shape; and
       a second light source configured to illuminate the surface of the subject's body from a second angle, the second angle different than the first angle, wherein the second light source generates a second set of lighted features, wherein the second set of lighted features comprise a second shape distinguishable from the first shape;
       wherein each of the one or more of the lighted features within the first set of lighted features and the second set of lighted features can be displaced in any direction a distance from a starting position to a displaced position on the subject's body in response to a vibratory signal from the subject's body; and
    a control circuit configured to
       receive input from the subject body analysis system including spatial vibration as a function of location on the surface of the subject's body; and
       calculate a location for implanting a medical device based on the spatial vibration as a function of location on the surface of the subject's body.

13. A method of evaluating body vibrations comprising:
    illuminating a surface of a subject's body from a first angle with a first set of lighted features, wherein one of the lighted features within the first set of lighted features is displaced in a first displacement direction relative a first starting position on the subject's body in response to a vibratory signal from the subject's body;
    illuminating a surface of a subject's body from a second angle with a first set of lighted features, wherein one of the lighted features within the second set of lighted features is displaced in a second displacement direction relative a second starting position on the subject's body in response to the vibratory signal from the subject's body;

detecting light reflected from the surface of the subject's body; and calculating spatial vibration as a function of location on the surface of the subject's body based on the detected light;

wherein a magnitude of relative displacement of the first displacement direction is compared to a magnitude of relative displacement of the second displacement direction to derive a magnitude of vibration at a site of the first lighted feature within the first set of lighted features and the second lighted feature within the second set of lighted features; and wherein the first lighted features comprise a first shape and the second lighted features comprises a second shape, wherein the first shape is different than the second shape.

14. The method of claim 13, wherein the first set of lighted features are at least one of a different color than the second set of lighted features and a different intensity than the second set of lighted features.

15. The method of claim 13, further comprising generating a body surface map as a function of determined spatial vibration.

16. The method of claim 13, wherein the first angle and the second angle intersect at an angle of about 10 to 45 degrees.

17. The method of claim 13, further comprising calculating a location for sensing vibrations within a particular frequency range based on the determined spatial vibration as a function of location on the surface of the subject's body.

18. The method of claim 13, further comprising averaging spatial vibration as a function of location on the surface of the subject's body over a plurality of physiological vibration cycles.

19. The method of claim 13, further comprising using a signal from a sensor to separate and align spatial vibration data representing different physiological vibration cycles, the sensor comprising an ECG sensor.

* * * * *